United States Patent
Hajduk et al.

(10) Patent No.: US 7,047,794 B2
(45) Date of Patent: May 23, 2006

(54) TETHER PLATE SENSOR FOR MEASURING PHYSICAL PROPERTIES OF FLUID SAMPLES

(75) Inventors: Damian Hajduk, San Jose, CA (US); Eric Carlson, Cupertino, CA (US); Ravi Srinivasan, Santa Clara, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/090,755

(22) Filed: Mar. 25, 2005

(65) Prior Publication Data

US 2005/0166667 A1    Aug. 4, 2005

Related U.S. Application Data

(60) Division of application No. 10/712,617, filed on Nov. 12, 2003, which is a continuation of application No. 10/205,060, filed on Jul. 25, 2002, now Pat. No. 6,668,622, which is a continuation of application No. 09/632,378, filed on Aug. 3, 2000, now Pat. No. 6,484,567.

(51) Int. Cl.
*G01N 11/10*    (2006.01)

(52) U.S. Cl. .................. 73/54.37; 73/54.23; 73/54.38; 73/54.39; 73/54.28

(58) Field of Classification Search ............... 73/54.01, 73/54.23, 54.24, 54.27, 54.37, 54.38, 54.39, 73/54.41
See application file for complete search history.

(56) References Cited

U.S. PATENT DOCUMENTS

| 4,343,190 A | 8/1982 | Danko et al. |
| 4,361,026 A | 11/1982 | Muller et al. |
| 4,567,774 A | 2/1986 | Manahan et al. |
| 4,602,501 A | 7/1986 | Hirata |
| 4,794,788 A | 1/1989 | Masters et al. |

(Continued)

FOREIGN PATENT DOCUMENTS

JP    55-65136    11/1980

(Continued)

OTHER PUBLICATIONS

Braithwaite, Gavin J.C. and McKinley, Gareth H., "Microrheometry For Studying The Rheology and Dynamics of Polymers Near Interfaces," Appl. Rheol. 9, 1, 27-33 (1999).

(Continued)

*Primary Examiner*—Daniel S. Larkin
(74) *Attorney, Agent, or Firm*—Dobrusin & Thennisch PC

(57) ABSTRACT

The present invention relates to a miniature rheometer, a parallel rheometer, and improved force sensor elements which may advantageously be used in combination with the miniature rheometer and the parallel rheometer. The miniature rheometer is adapted to determine rheological characteristics of materials which are provided in the form of small quantity samples. The miniature rheometer comprises an actuating element, a sensing element and a feedback circuit to provide rebalance of the shear force applied by the sample to the sensing element, which insures an exceptional stiffness in determining the shear strain so as to allow measurements of high accuracy. The parallel rheometer of the present invention allows simultaneous measurements of a plurality of samples so as to allow of a plurality of samples within a short time period. The force sensor element according to the present invention allows simultaneous measurement of a shear force and a normal force applied to the sensor element. Moreover, a rheometer is provided which comprises a force sensor based on stress-optic material.

11 Claims, 6 Drawing Sheets

U.S. PATENT DOCUMENTS

| | | |
|---|---|---|
| 4,854,175 A | 8/1989 | Budhu |
| 4,896,098 A | 1/1990 | Haritonidis et al. |
| 4,941,346 A | 7/1990 | Suzuki et al. |
| 5,052,228 A | 10/1991 | Haritonidis |
| 5,089,696 A | 2/1992 | Turpin |
| 5,199,298 A | 4/1993 | Ng et al. |
| 5,233,213 A | 8/1993 | Marek |
| 5,253,513 A | 10/1993 | Van Arsdale et al. |
| 5,271,266 A | 12/1993 | Eschbach |
| 5,277,058 A | 1/1994 | Kalyon et al. |
| 5,314,572 A | 5/1994 | Core et al. |
| 5,326,726 A | 7/1994 | Tsang et al. |
| 5,345,824 A | 9/1994 | Sherman et al. |
| 5,356,756 A | 10/1994 | Cavicchi et al. |
| 5,357,783 A | 10/1994 | Eschbach |
| 5,374,792 A | 12/1994 | Ghezzo et al. |
| 5,417,111 A | 5/1995 | Sherman et al. |
| 5,454,904 A | 10/1995 | Ghezzo et al. |
| 5,504,026 A | 4/1996 | Kung |
| 5,511,428 A | 4/1996 | Goldberg et al. |
| 5,610,325 A | 3/1997 | Rajagopal et al. |
| 5,623,096 A | 4/1997 | Bandyopadhyay |
| 5,659,195 A | 8/1997 | Kaiser et al. |
| 5,750,884 A | 5/1998 | Field |
| 5,883,310 A | 3/1999 | Ho et al. |
| 5,943,223 A | 8/1999 | Pond |
| 5,948,993 A | 9/1999 | Ting et al. |
| 5,985,356 A | 11/1999 | Scuhltz et al. |
| 6,023,962 A | 2/2000 | Wang et al. |
| 6,151,123 A | 11/2000 | Nielsen |
| 6,157,449 A | 12/2000 | Hajduk |
| 6,182,499 B1 | 2/2001 | McFarland et al. |
| 6,196,059 B1 | 3/2001 | Kosslinger et al. |
| 6,331,438 B1 | 12/2001 | Aylott et al. |
| 6,336,353 B1 | 1/2002 | Matsiev et al. |
| 6,341,532 B1 | 1/2002 | Xu et al. |
| 6,393,898 B1 | 5/2002 | Hajduk et al. |
| 6,484,567 B1 * | 11/2002 | Hajduk et al. .............. 73/54.37 |
| 2002/0194906 A1 | 12/2002 | Goodwin et al. |

FOREIGN PATENT DOCUMENTS

| | | | |
|---|---|---|---|
| WO | WO 96/14930 | 5/1996 | |
| WO | WO 00/36410 | 6/2000 | |
| WO | WO 02/077613 A2 * | 10/2002 | ................ 73/54.42 |

OTHER PUBLICATIONS

Fruh, S.M. et al., "Recoverable Shear Measurements in a Parallel Plate Rheometer", A1ChE Journal, vol. 16, No. 6, Nov. 1970, pp. 907-910.

Schmidt, Martin A., et al., "Design and Calibration of a Microfabricated Floating-Element Shear-Stress Sensor," IEEE Transactions on Electron Devices, vol. 35, No. 6, 750-757 (1988).

Shajii, Javad, et al., "A Microfabricated Floating-Element Shear Stress Sensor Using Wafer-Bonding Technology," Journal of Microelectromechanical Systems vol. 1, No. 2, 89-94 (1992).

\* cited by examiner

TETHER PLATE SENSOR FOR MEASURING PHYSICAL PROPERTIES OF FLUID SAMPLES

CLAIM OF PRIORITY

This application is a division of Ser. No. 10/712,617 filed on Nov. 12, 2003, which is a continuation of Ser. No. 10/205,060 filed on Jul. 25, 2002, now U.S. Pat. No. 6,668,622 which is a continuation of Ser. No. 09/632,378 filed on Aug. 3, 2000, now U.S. Pat. No. 6,484,567.

TECHNICAL FIELD

The present invention relates to apparatus and methods for measuring physical properties of samples when subjected to an external shear force.

BACKGROUND

Producing materials having specific required properties is steadily gaining in importance and, hence, the field of combinatorial chemistry, which generally refers to methods for creating collections of diverse materials or compounds, commonly known as libraries, is steadily increasing and has revolutionized the process of drug discovery. Combinatorial chemistry enables researchers to rapidly discover and optimize useful materials such as polymers, superconductors, magnetic materials, etc. In order to record the various properties of the materials obtained by combinatorial chemistry, it is necessary to precisely and efficiently determine the characteristics of the materials, preferably under varying environmental conditions. One important and useful characteristic is the behavior of a material, in particular of a polymer, when exposed to an eternally-applied shear force. Instruments for measuring the response of fluids to applied shear are generally referred to as Theological instruments, which may be subdivided into indexers and rheometers. Indexers measure a quantity which is correlated with the rheological characteristics, but which is difficult to analyze in terms of intrinsic material properties. Although indexers can be assembled rapidly from commercially available components, the results of measurements carried out by means of such indexers are difficult to relate to results of measurements from other indexers, or to intrinsic material properties, without extensive calibration.

Rheometers, on the other hand, measure intrinsic material characteristics, giving them broad applicability. Such generality, however, comes at a price due to design costs and complexity which are dictated primarily by the need for well-defined static and dynamic test conditions. Moreover, these known rheometers require fairly large quantities of sample in the order of 500 mg so as to obtain the required accuracy in analyzing the samples. Such large quantity samples, however, are usually not provided by combinatorial synthesizing methods in which, generally, a large amount of differing samples of small quantity are produced.

Rheological measurements on sample materials, such as polymeric materials, are performed in their simplest geometry such that the sample is placed between two parallel plates of a design area separated by a gap of known distance, wherein the sample is sheared by applying a force to one of the plates while keeping the other plate fixed. This results in a displacement, i.e. a deformation of the sample confined between the plates, which can be characterized in terms of the shear stress and the shear strain. From these quantities and the dimensions of the sample, a shear modulus may be calculated. In general, the shear modulus is a function of the sample history, the shear strain and the strain rate. For polymeric materials, the temporal dependence of the shear modulus at constant stress typically exhibits four different regimes reflecting different relaxation mechanisms available to the polymer chain.

For sufficiently small deformations, most polymers exhibit linear viscoelastic behavior in which the shear modulus is independent of the shear strain. Theories of polymer dynamics generally explain the response of a chain in terms of normal modes, each having a characteristic frequency. The linear viscoelastic theory gives, then, the response of the material as a function of shear history. In measuring the mechanical property of a sample material, the sample is subjected to a varying force, e.g. a sinusoidal-varying force, and the resulting deformation, i.e. the response of the sample is observed. The frequency response of the sample may then be analyzed in accordance with viscoelastic theories to obtain information on the required characteristic of the material.

In order to perform these measurements with a high degree of accuracy, the rheological apparatus must be capable of producing a well-defined displacement within a specified frequency range. Additionally, since each frequency corresponds to probing the response of the sample material at a particular relaxation time, such measurements take a relatively long time period when the relaxation mechanism of the samples requires the employment of low frequencies. Hence, measuring a plurality of samples which may be produced by combinatorial chemistry is a very time-consuming and therefore very expensive procedure.

Moreover, the performance of accurate measurements requires the application of suitable sensor elements for detecting the shear stress in the samples. In order to obtain meaningful experimental results, the sensor elements have to be suitably designed so as to reflect the response of the sample to the applied shear strain without any interference or at least minor interference of the sensor element.

In view of the above-mentioned problems, it is an object of the present invention to provide apparatus and methods for rheological measurements which are capable of producing reliable measurement results for a plurality of small quantity samples within a short time period.

SUMMARY OF THE INVENTION

According to one aspect of the present invention, there is provided a miniature rheometer for analyzing a small quantity sample of a material of interest, wherein the rheometer comprises a first plate and a second plate, forming a pair of plates having a known geometry for confining the sample between the plates, said sample having a volume of 200 microliters or less; an adjusting device for adjusting the separation of the plates; an actuating element mechanically coupled to the first plate, which produces a shear strain within the sample by generating a defined small-scale relative motion of the first and second plates; a sensing element which outputs a position signal indicative for a displacement of at least one of the first and second plates; and a feedback circuit for providing force rebalance of the force, applied to the sample by the small-scale relative motion of the first and second plates, on the basis of the position signal, wherein an amount of force rebalance is a measure for the stress within the sample.

The miniature rheometer according to the present invention is suitably adapted to characterize combinatorial materials. In contrast to known instruments which generally require large sample volumes, typically 10–100 times the quantity produced by current combinatorial synthetic approaches, the present invention merely requires sample quantities having a volume of 200 microliters or less, or preferably 10–50 microliters, which are easily obtained by combinatorial synthesizing methods. Since measurements on such small sample volumes requires an accurate response of the rheometer on a corresponding small length scale, the present invention provides a sensing element and a feedback circuit which provide for force rebalance of the force that is applied to the sample in order to avoid the undesired inherent displacement of conventional force sensor elements due to shear forces exerted by the sample on the force sensor. Accordingly, the force balance may be controlled such that the present miniature rheometer exhibits an extremely high effective stiffness with respect to the sample, which in turn insures accurate measurement results, even at very small displacements.

In further embodiments, the position signal which is input into the feedback circuitry so as to adjust the force rebalance is obtained from the sensing element which may comprise a deformation-sensing element, an encoder means, or any other appropriate means suitable to determine the location of the plates with a spatial resolution that is substantially smaller than a minimal displacement of the plates as required for the desired measurement accuracy. The rheometer may comprise a sensor-actuating element that is mechanically coupled to the second plate so as to maintain the second plate at a predefined position upon reception of a driving signal from the feedback circuit. Alternatively, the actuating element may be driven from the feedback circuit such that the first plate maintains a desired displacement, wherein the second plate may be a fixed plate or may be kept at a fixed position.

In a further embodiment, the actuating element used as a shear strain producing means comprises a piezo-electric actuator so as to produce the small-scale relative motion. This allows the miniature rheometer to create small relative displacements of the plates while insuring easy control and configuration of the actuator.

In a further embodiment, the plates are disposable plates. The employment of disposable plates may considerably facilitate sample preparation and sample replacement after completion of a measurement run.

Advantageously, the deformation sensing element is coupled to the actuating element or the sensor-actuating element or to both and detects a deformation of at least a portion of the respective actuating element. The deformation sensing element measures the amount of deformation generated by the shear force applied to the sample. In this manner, the signal from the deformation sensing element may either be directly used as a measure for the shear force, or it may be supplied to the feedback circuit which adjusts the force exerted on the deformation sensing element by the actuating element or the sensor-actuating element so as to return the deformation sensing element to a predefined location, e.g. the undeflected state of the deformation sensing element.

In a further embodiment, two or more miniature rheometers may be arranged so as to form a parallel rheometer for simultaneously measuring two or more small quantity samples. To this purpose, a common control unit is provided which controls the shear strain producing means and the force sensors of the two or more miniature rheometers.

According to a second aspect of the present invention, there is provided a parallel rheometer for simultaneously analyzing material characteristics of two or more samples, wherein the parallel rheometer comprises first and second plates respectively having regions for receiving and confining said two or more samples, the first and second plates being moveable relative to each other; an actuator adapted to move the first and second plates relatively to each other for producing a shear strain within each sample; and at least one sensor associated with each region for simultaneously detecting shear stress within each sample.

As previously stated, standard Theological measurements often characterize materials according to their frequency response to an applied oscillatory shear force. Here, the frequencies of interest set the minimum measurement time required, which is typically three or four times the reciprocal of the frequency. Thus, by allowing the simultaneous measurement of a large number of samples by means of a parallel rheometer according to the present invention, a quick screening of a plurality of material samples (such as those produced by combinatorial synthetic approaches) is feasible. Moreover, according to the present invention, the minimum sample volume may be kept smaller than in known single-channel rheometers so as to permit measurements as a function of environmental conditions to use much faster condition change rates than are possible with large samples. To this end, the parallel rheometer as well as the miniature rheometer may comprise means for applying varying environmental conditions. Preferably, the environmental conditions to be varied, individually or simultaneously in any combination, at least include temperature, pressure at a fixed gas composition, composition of a gas atmosphere surrounding the sample, electric field, magnetic field, and time of application of one or more of the preceding quantities when adjusted to respective predetermined values. The means may be designed so as to allow the variation of the environmental conditions individually for each sample and/or simultaneously for a group of samples.

In a further embodiment, the shear stress detector comprises a micromachined sensor element at each sample position. This allows mass production of nearly identical sensor elements at low cost, wherein the required sample volume may easily be maintained relatively small due to the reduced sensor mass and increased sensitivity provided by micromachined devices.

According to a third aspect of the present invention, there is provided a rheometer, comprising:
a pair of plates spaced apart from each other by a defined distance for receiving and confining a sample therebetween, an adjusting means which adjusts the distance between the plates, a driving means coupled to at least one of the plates, which generates a relative motion between the plates without changing the distance, and a shear stress sensor, the shear stress sensor comprising a stress-sensing material of a defined stress-optic coefficient indicating one of birefringence and retardation of linearly polarized light passing the stress-sensing material, as a function of applied stress/unit path length.

The shear stress detector comprises a stress-optical sensor element which is insensitive to electric and magnetic fields, and thus allows to analyze samples within such fields without creating electrical noise.

According to a fourth aspect of the present invention, there is provided a sensor element for outputting a signal in response to a mechanical deformation applied to the sensor element, wherein the sensor element comprises: a sample plate arranged within an opening of a substrate; at least two tethers, one of each tether being attached to the sample plate, the other end of each tether being attached to the substrate so as to support the sample plate; a piezo-resistive portion in each of the tethers; and a wiring line formed on the tethers and the substrate, connecting each piezo-resistive portion with a corresponding contact pad formed on the substrate, wherein the piezo-resistive portion of one of said at least two tethers is adapted to generate a maximum change of its internal resistance when a shear force is applied to the sample plate, and wherein the piezo-resistive portion of the other one of said at least two tethers is adapted to generate a maximum change of its internal resistance when a force normal to the sample plate is applied.

As is generally known, shearing a viscoelastic material also generates a force along the shear gradient direction. Such forces are potentially of either sign and can be comparable in magnitude to the shear force. They can strongly affect the macroscopic flow properties of a material. At a minimum, rheometers must be sufficiently stiff in the shear gradient direction so that shear actuation results in as near a pure shear field as possible, and that any strain determination measures only the shear strain. By means of the sensor element provided according to the third aspect of the present invention, a shear force and a normal force applied to a sample can be detected simultaneously. This improves the accuracy of the measurement results due to separation of the total instrumental response into shear and normal force components and provides a more comprehensive picture of the response of the sample to applied shear.

This sensor element is particularly advantageous when used in combination with the above parallel rheometer.

Further advantages and objects of the present invention follow from the dependent claims and the detailed description of the preferred embodiments.

DETAILED DESCRIPTION OF THE PREFERRED EMBODIMENTS

Figure 1:
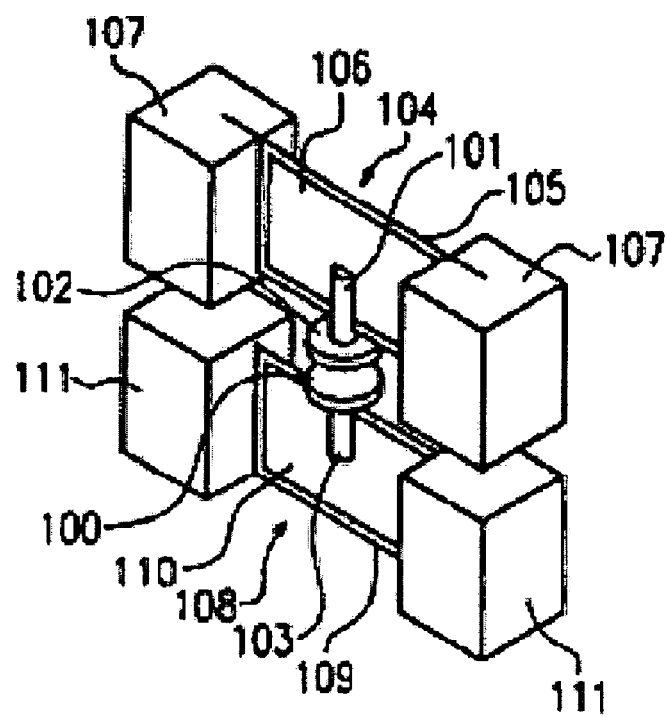
FIG. 1 is a schematic perspective view of a translational embodiment of the miniature rheometer according to the present invention.

With reference to FIGS. 1 and 2, a translational embodiment, i.e. an embodiment that produces a translational displacement between a top surface and a bottom surface of a sample, of the miniature rheometer according to the present invention will now be described in detail.

In FIG. 1, merely a portion of the translational embodiment of the miniature rheometer of the present invention is shown. A moving plate 102 is mounted on a shaft 1101. Another plate 100, which will also be referred to as the "fixed plate" even though this plate may be movable, is arranged parallel to the moving plate 102. Plates 100 and 102 have surfaces which are arranged in an opposed relationship so as to be parallel to each other. The geometrical structure as well as the dimensions of the respective surfaces are selected so as to result in a desired configuration. Although the plates 100 and 102 are shown as circular elements, any other geometrical structure, such as squares or rectangles, etc., may be used for the surfaces of plates 100 and 102. Plate 100 is also mounted on a shaft 103. Preferably, the shafts 101 and 103 are made of a rigid, thermally insulating material. However, any appropriate material may be used, and in some cases electrical and/or thermal conductivity of portions of the shaft 101 and 103 may be desirable. Shaft 101 is attached to an actuating element 104, which comprises a metal foil 105 which is of a rectangular shape. On at least one side of the metal foil 105, a plate of piezoelectric material 106 is attached. In this embodiment two piezoelectric plates 106 are used with the metal foil 105, however, it is also possible to use merely one piezoelectric plate on one surface of the metal foil 105. Moreover, two or more piezoelectric plates may be used in accordance with design requirements. Actuating element 104 is attached to shaft 101, preferably in a non-permanent manner, e.g. by providing a slit for receiving the actuating element 104. This permits the use of disposable plates, which in turn facilitates measurements of samples that are difficult to remove from the plates. The actuating element 104 is further attached to a mechanical assembly, which may be provided in the form of clamping blocks 107 which comprise slits for receiving end portions of the actuating element 104. A wiring assembly for applying a voltage to the piezoelectric plates 106 is also provided, but is not shown in FIG. 1. Depending on the crystallographic orientation of the piezoelectric plates 106, metal foil 105 may serve as a common electrode for applying a desired voltage to the plates 106. Alternatively, metal foil 105 may be covered by a thin, electrically-insulating layer on the middle portion, where the piezoelectric plates 106 cover the metal foil so that a voltage may be applied to the piezoelectric plates 106 by means of the electrically conductive end portions of the metal foil 105, which are clamped in place by a clamping blocks 107, which then preferably may be made of an electrically conductive material so as to serve as electrodes.

In this embodiment, the assembly regarding the fixed plate 100 is identical to the structure referring to moving plate 102, i.e. shaft 103 is attached to an actuating element 108 comprising a metal foil 109 with piezoelectric plates 110 on either side. Clamping blocks 111 are provided in order to clamp the actuating element 108 in place. Regarding electrical connections to the piezoelectric plates 110, the wiring is configured in an analogous manner as previously described with reference to plates 106.

Figure 2A:
FIGS. 2a–2c are schematic top views of actuator elements shown in FIG. 1.

FIG. 2a is a schematic top view of the actuating element 104 or of the actuating element 108 of FIG. 1. For the sake of clarity only, the reference signs regarding actuating element 104 are shown. As the piezoelectric plates 106 are made of a piezoelectric material, the plates 106 will undergo dimensional changes in response to an applied electric field. In FIG. 2a, the piezoelectric plates 106 are arranged such that the application of a voltage of known polarity will cause an expansion of the upper one of the piezoelectric plates 106 along a longitudinal axis and application of the reverse voltage to the lower piezoelectric plates will cause a contraction of the plate along the longitudinal axis as indicated by corresponding arrows in the figure.

Figure 2B:

FIG. 2b shows the actuating element 104 in the state when a voltage is applied.

Figure 2C:
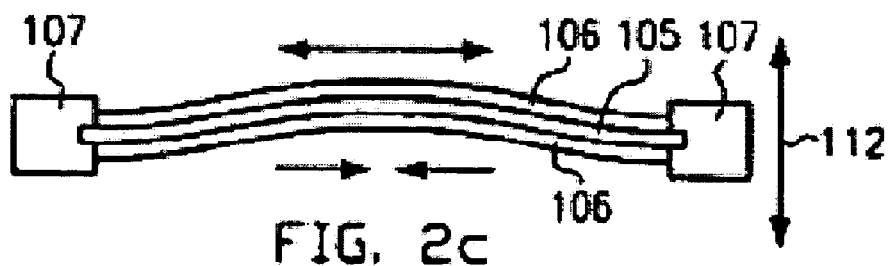

FIG. 2c schematically shows the bent actuating element 104, when the end portions thereof are clamped in place by the clamping blocks 107. The application of a voltage to the clamped actuating element 104 produces a quadruple bend that is symmetric about the center portion of the actuating element. Reversing this voltage reverses the bend. Application of an alternating voltage to the actuating element 104 therefore results in reciprocating linear translation of the center of the actuating elements as is indicated by arrow 112.

In operation, a sample of a material of interest, preferably a material produced by combinatorial synthetic approaches, is disposed in the gap between the moving plate 102 and the fixed plate 100. In order to obtain well-defined experimental conditions, means may be provided to remove excess sample material, which may have accumulated during sample loading, from the edges of the plates. This is typically accomplished by providing a sharpened punch which translates and/or rotates along the plate edges so as to cut away excess material which extends beyond the edges of the plates. After having arranged the samples, which can be prepared by molding or otherwise forming samples to the dimensions of the plates 100 and 102, the plates 100 and 102 are translated so as to be brought into contact with the formed sample. For this purpose, means are used which is not shown in the figures, but, which may, as the person skilled in the art will readily appreciate, be any appropriate mechanical assembly used in this field for translating the plates along a line normal to the opposing surfaces of the plates, so as to correctly adjust and define the distance of the gap. Alternatively, material may be placed on one plate and the other plate may be translated to a defined relative gap distance in order to mold specimens of known thickness. In this case, excess sample material is removed as previously pointed out.

Next, a defined voltage is applied to the actuating element 104, preferably an alternating voltage with known rate and amplitude, so as to achieve a desired displacement of the middle portion of the actuating element 104, as has been explained with reference to FIGS. 2a–2c. Thus, plate 102 which is coupled to the middle portion of the actuating element 104 by the rigid shaft 101 is also reciprocally displaced.

As previously mentioned, the actuating element 108 may be constructed in the same way as the actuating element 104. In this embodiment, the actuating element 108 serves as a force sensor detecting the force which is required to hold plate 100 in place. For this purpose, preferably one of the piezoelectric plates 110 acts as an actuating element, whereas the other one of the piezoelectric plates 110 serves as a deformation sensor element. As can be readily appreciated, both piezoelectric plates 110 may serve as an actuating element and an additional deformation sensor element. The deformation sensor element may be a piezoelectric plate or a conventional mechanical deformation sensor, such as a strain gage, attached to actuating element 108. The middle portion of actuating element 108 will be displaced in response to the shear force applied to the sample confined between the plates 100 and 102. This displacement is detected by one of the piezoelectric plates 110 or, alternatively, by an additionally applied deformation sensing element, and is output as an electrical signal to a feedback circuitry which is not shown in the figures. The feedback circuitry, in turn, will supply a voltage to the piezoelectric plate 110 which serves as an actuating element, so as to generate a force which opposes the shear force applied by the sample to the plate 100. Accordingly, the feedback circuitry may be controlled such that the actuating element 108, and thus the plate 100, may be maintained in an un-deflected state or any desired position when an offset voltage is added to the voltage supplied to piezoelectric plate 110. Advantageously, the voltage applied to the piezoelectric plate 110, which serves as an actuating element, may also serve as an output of the force sensor for determining the shear force within the sample. In comparison with traditional force sensors, this "force rebalance" sensor is exceptionally stiff, i.e. the fixed plate 100 remains fixed for a wide range of applied shear forces, and hence it is possible to accurately determine the shear strain, i.e. the difference in the lateral position between the moving plate 102 and the fixed plate 100.

The output of the force sensor, i.e. the actuating element 108, may then be processed in any desired manner, i.e. the voltage obtained from the force sensor may be amplified, converted into digital signals, stored in a corresponding memory, or processed by a microprocessor so as to receive required force—displacement curves, which can be related to various Theological or mechanical characteristics of the sample, wherein the dimensions of the plates 100 and 102 are taken into account. In a typical application for polymeric materials, the moving plate 102 executes sinusoidal varying motions with frequencies from 0.01–1000 rad/s with an amplitude of, at most, 1% of the spacing between the plates 100 and 102. The sinusoidally-varying signal is observed at the force sensor, wherein the ratio of force waveform amplitude to the displacement waveform amplitude is related to the modulus of the material at that frequency. The existence of a difference in phase between the force and displacement waveforms implies that this modulus may be represented as a complex quantity. The real part of this complex modulus corresponds to the "elastic" or "storage" modulus of the viscoelastic material; the imaginary part corresponds to the "viscous" or "loss" modulus.

Although the above embodiment is described using the piezoelectric actuator 104, it is also possible to employ any appropriate means for displacing the sample, such as a motorized stage, which then may preferably include a second force sensor for determining any force exerted along a line joining the centers of the moving plate 102 and the fixed plate 100 when the plates are positioned above one another. This type of force is usually referred to as normal force. A variety of force sensors are suitable for this purpose, in particular the piezoelectric force sensor as described above.

Figure 3:
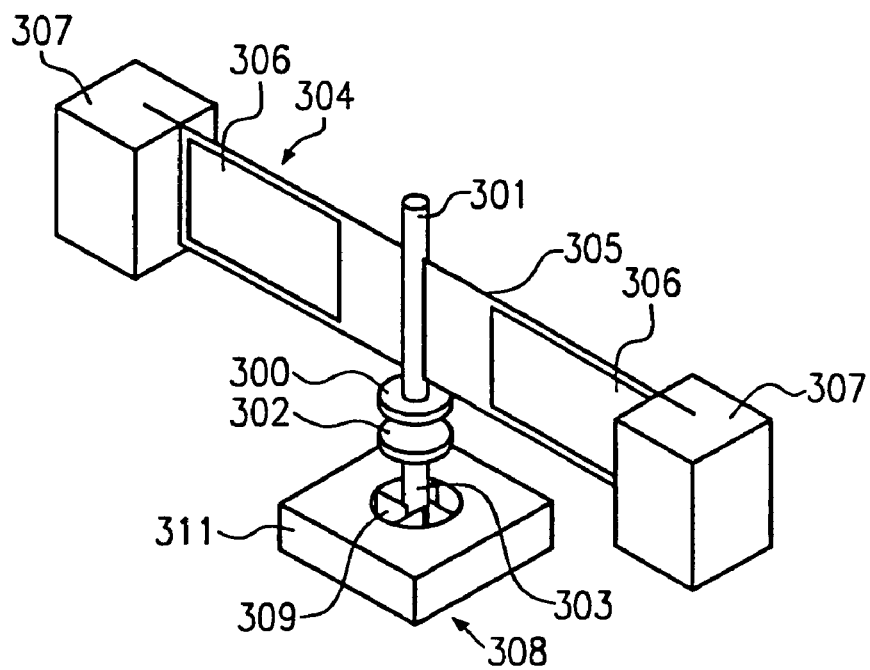
FIG. 3 is a schematic perspective view of a rotational embodiment of the miniature rheometer according to the present invention.
Figure 4:
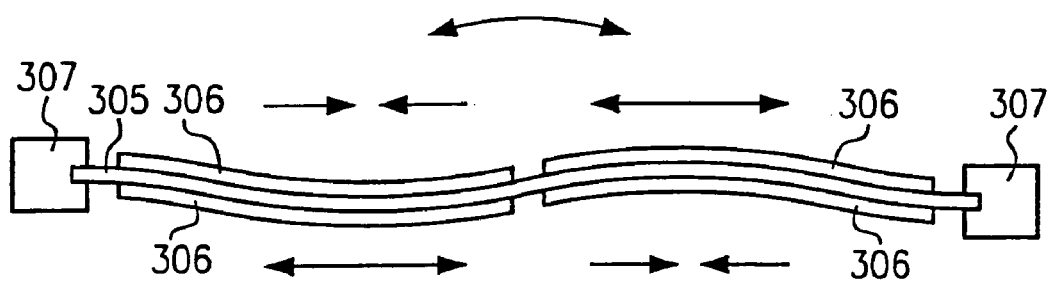
FIG. 4 is a schematic top view of an actuator element as shown in FIG. 3.

With reference to FIGS. 3 and 4, a further embodiment is described which is capable of generating a rotational displacement with respect to the surfaces of a small quantity sample.

FIG. 3 shows a perspective schematic view of a rotational embodiment of the present invention.

Between a moving plate 300 and a fixed plate 302, a small quantity sample of a material to be characterized may be arranged. Regarding the preparation of the sample and adjusting the distance between the plates 300 and 302, the same considerations as given with respect to the translational embodiment shown in FIG. 1 also apply in this case. Moving plate 300 is mounted on a shaft 301 which, in turn, holds an actuating element 304. Actuating element 304 is comprised of a metal foil 305 of rectangular shape. Attached to metal foil 305 are four piezoelectric plates 306, wherein two of the piezoelectric plates 306 are arranged on one surface of the metal foil separated by the shaft 301 and the other two of the piezoelectric plates 306 are arranged on the other surface of metal foil 305. Thus, two of the respective piezoelectric plates 306 are arranged in an opposed relationship with metal foil 305 disposed in-between. The metal foil 305 is clamped in place by a mechanical assembly provided as clamping blocks 307.

Fixed plate 302 is mounted on a shaft 303 which, in turn, is connected to a torque sensor 308 which comprises sensor elements 309 that are connected with one end portion to the shaft 303, and with the other end portion to a support 311.

FIG. 4 shows a schematic top view of the actuating element 304. Similarly, as already explained with reference to FIGS. 2a–2c, two opposing piezoelectric plates 306 sandwiching the metal foil 305 are electrically connected to a voltage supply in such a way that application of a voltage leads, for example, to an expansion of the upper piezoelectric plate and a contraction of the lower piezoelectric plate on the right side of FIG. 4, and the piezoelectric plates 306 on the left side are accordingly wired so as to exhibit the inverse behavior. Thus, a central axis of the metal foil perpendicular to the drawing plane of FIG. 4 is subjected to a rotational displacement.

Figure 5:
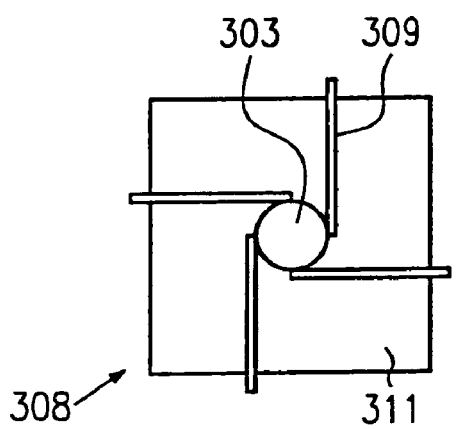
FIG. 5 is a schematic top view of a force sensor which may be used in the rotational embodiment as shown in FIG. 3.

FIG. 5 shows a schematic top view of the torque sensor 308. The shaft 303, which may be made of a thermally insulating material, is attached, preferably in a non-permanent manner so as to permit the use of disposable plates, to at least two piezoelectric plates. In the present case, however, four piezoelectric plates 309 are employed and are attached to the surface of the shaft 303, such that one end of each piezoelectric plate 309 is tangential to the surface of the shaft 303. The other end of each piezoelectric plate is tethered to the rigid support 311. The crystal structure of plate 309 is aligned such that applying a voltage across the plate causes the greatest dimensional change along the line tangential to the shaft 303. As is shown, the piezoelectric plates 309 are preferably aligned along opposite sides of the shaft 303 so that the net torque resulting from application of a voltage across the piezoelectric plates does contain a component which would tend to rotate the shaft out of its un-energized orientation.

The torque sensor 308 further contains a sensing element, in this case in the form of the other two of the piezoelectric plates 309. The sensing element may, however, be any conventional strain gage or piezoelectric element which generates a signal upon rotation of the shaft 303. A feedback circuit which is not shown in the figure monitors this signal and adjusts the voltage applied to the piezoelectric plates 309, which act as an actuating element, so as rebalance the force applied to the shaft 303 and to return the shaft 303 to the un-rotated position or any desired position when a corresponding offset voltage is added to the voltage supplied to the piezoelectric plates 309. Advantageously, this voltage may also serve as a measure of the torque at the shaft 303.

As in the case of the translational embodiment, this design is exceptionally stiff so that the fixed plate 302 remains fixed for a wide range of supplied shear forces. Hence, the torque sensor as described above permits the shear strain, i.e. the difference in angular position between the moving plate 300 and the fixed plates 302, to be accurately determined.

Figure 6:
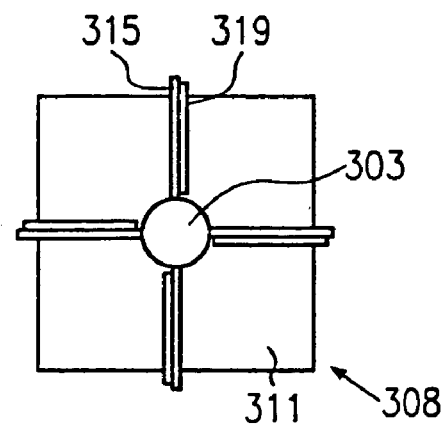
FIG. 6 is a schematic top view of a further force sensor, which may be used with the rotational embodiment as shown in FIG. 3.

FIG. 6 shows an alternate form of the torque sensor. In this alternative embodiment, the torque sensor 308 comprises two or more piezoelectric assemblies, each consisting of at least one piezoelectric plate 319 bounded to a metal foil 315, which are attached to the surface of the rigid shaft 303 such that one of the edges of the foil is parallel to the axis of the shaft 303 and that the other edge of the foil lies along a line perpendicular to the axis of the shaft. The edge of metal foil 315 opposite the edge in contact with shaft 303 is clamped in place by means of the rigid support 311. In the embodiment described with reference to FIG. 5, applying a voltage to the piezoelectric plates produces the expansion or contraction of the assembly along a line tangential to the shaft 303, resulting in a torque. In this alternative embodiment, applying a voltage to the piezoelectric assembly comprising the piezoelectric plate 319 and metal foil 315 produces the buckling of the metal foil 315 and thus the rotation of the "shaft end" of the assembly about the "clamped end", also resulting in a torque being applied to the shaft 303. In this embodiment, four piezoelectric assemblies, each comprising a piezoelectric plate and a metal foil are employed. As it will be readily appreciated, more than one piezoelectric plate 319 per piezoelectric assembly may be used. Moreover, any number of piezoelectric elements may be employed, wherein advantageously at least one of the piezoelectric assemblies may be used as a deformation sensing element in combination with a feedback circuit so as to maintain the shaft 303 on its un-rotated position, thereby providing an exceptionally stiff torque sensor element.

Sample preparation and operation of the rotational embodiment is carried out in a similar way as described with reference to the translational embodiment. Although moving plate 300 and fixed plate 302 have been described as plates with flat surfaces, any appropriate geometry of the plate surface may be employed. For example, one of the plates may consist of a cone of known apex angle, which is well-known in the art as "cone and plate" geometry.

Furthermore, as already pointed out with reference to the translational embodiment, the shafts 301 and 303 are preferably made of a rigid, thermally insulating material so that varying the temperature of the sample disposed between the plates 300 and 302 would not be affected by the shafts 301 and 303 coupled to actuating element 304 and torque sensor 308, respectively. Moreover, the shafts 301 and 303 are preferably attached to the actuating element and the sensor element in a non-permanent manner so as to permit the use of disposable plates, thereby increasing the speed of sample replacement.

In a further variation, which is not shown in the figures, the rheometer comprises a first plate that is mechanically coupled to an actuating element such as actuating element 104 as previously described with reference to FIG. 1. However, any other appropriate actuating element which allows a translational or rotational displacement between the first and the second plates may be used. A sensing element such as a deformation sensing element as described with reference to FIGS. 1–6 may be employed to output a signal to a feedback circuit in response to the displacement of the first plate. The feedback circuit, in turn, outputs a voltage to the actuating element so as to return the actuating element to a predefined position, thereby effecting a force rebalance of the force applied to a sample confined between the first and second plates. The voltage provided to the actuating element may serve as an indication of the shear stress within the sample. As can be readily appreciated, the second plate can be maintained at a fixed position, either by a second actuating element coupled to the second plate, or a fixed support holding the second plate. While the former alternative provides for the possibility to perform measurements as described with reference to FIGS. 1–6 and in a way as described in this paragraph, with the same apparatus, the latter alternative obviates the necessity for a second actuating element.

Moreover, the displacement can be detected by any suitable encoder means, such as an optical sensor, etc. to provide the position signal for the feedback circuit. Additionally, all of the embodiments as described above may additionally comprise an environmental chamber so as to vary physical properties such as pressure, gas composition of an atmosphere surrounding the sample, temperature, electric and magnetic fields by providing, for example, electrodes and coils providing an electrical and magnetic field across the sample, etc. In addition, two or more of the above embodiments may be combined to form a rheometer "array" or a "parallel rheometer", wherein advantageously a central control unit is provided so as to monitor and control the performance of individual rheometer elements of the rheometer array. Thus, a large number of small quantity samples may be characterized within a short time period, wherein the exceptionally stiff force sensor elements provide for accurate measurement results, even for the small scale displacements required for these samples.

Next, with reference to FIGS. 7–12, a further embodiment of a rheometer is described which allows simultaneous measuring a plurality of samples.

Figure 7:
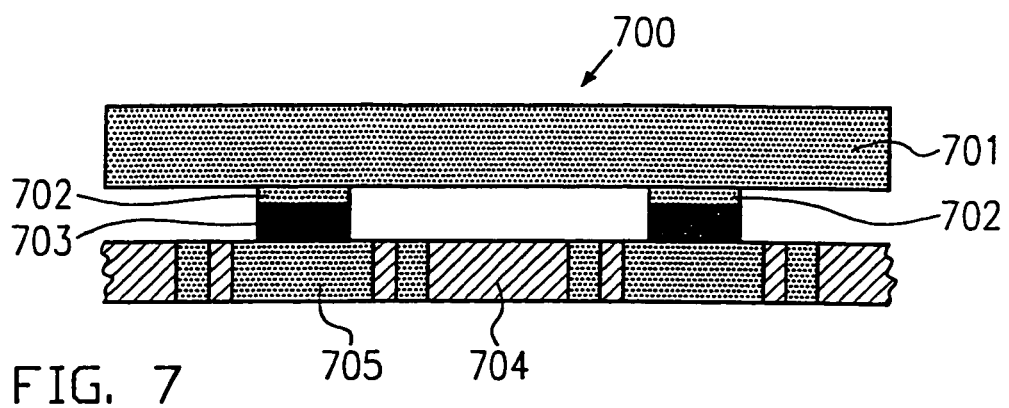
FIG. 7 is a schematic side view of an individual measurement element of a translational embodiment of the parallel rheometer using micromachined sensor elements.

FIG. 7 shows a schematic cross-sectional side view of an exemplary embodiment of the parallel rheometer of the present invention. In FIG. 7, a parallel rheometer 700 comprises a shear plate 701 which may contain, at predefined locations, raised regions 702 of known dimensions. Samples 703 are disposed between the shear plate 701 and a fixed plate 704 at the predefined regions. In this embodiment, the fixed plate 704 is made of an appropriate substrate carrying corresponding micromachined sensor elements. However, any appropriate fixed plate, preferably made of a rigid material such as aluminum or stainless steel, may be employed. The shear plate 701 and the fixed plate 704 are arranged parallel to one another with typical plate separations at the predefined regions of under 1 mm. With each predefined region, i.e. with each sample, there is associated a sensor element 705 in order to detect a force applied to the sensor element 705 by the shear plate 701 via the sample 703. Although in FIG. 7 a micromachined silicon force sensor is shown as the sensor element 705, any appropriate sensor may be employed, including those sensor elements that are described later with reference to FIGS. 10–12. The sensor element 705 has been micromachined in a silicon substrate, however any appropriate material such as silicon nitride and silicon dioxide may be used for the fixed plate 704 and the sensor elements 705.

Figure 8:
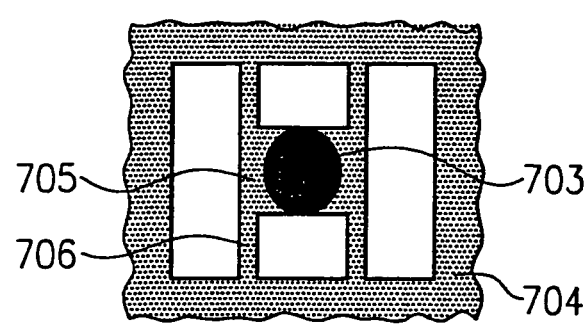
FIG. 8 is a schematic top view of the individual measurement element of the translational embodiment of the parallel rheometer as shown in FIG. 7.

FIG. 8 shows a schematic top view of one rheometer element with the shear plate 701 removed. The sample 703 is placed on a rectangular silicon plate of the force sensor element 705. The rectangular plate is attached to the fixed plate 704, i.e. in this case a silicon substrate, by means of four tethers 706. The tethers 706 are equipped with piezoelectric material or any other appropriate means for sensing a deformation of the tethers 706.

Figure 9:
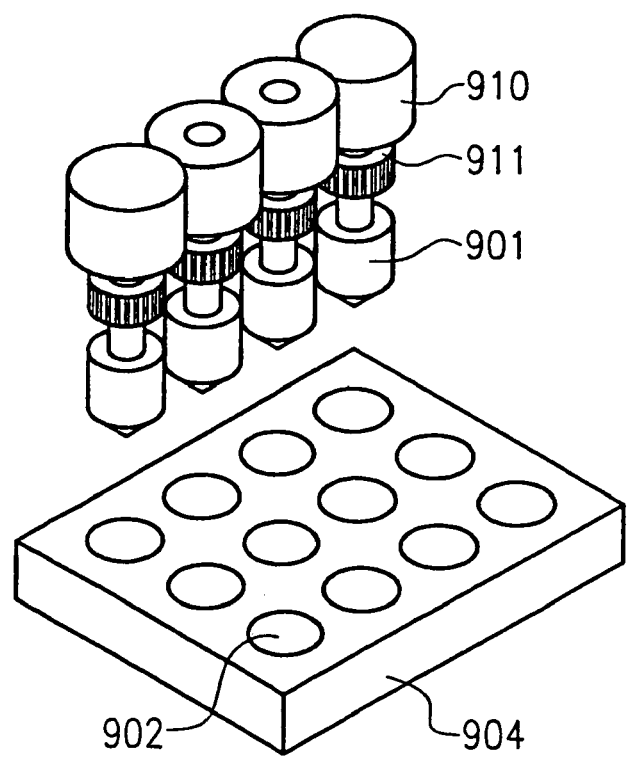
FIG. 9 is a schematic perspective of a rotational embodiment of the parallel rheometer according to the present invention.

FIG. 9 is a schematic perspective view of a further embodiment of the parallel rheometer according to the present invention. In FIG. 9, a fixed plate 904 comprises predefined regions 902 for receiving a sample of a material of interest. An array of test fixtures 901 is movably mounted on a means which is not shown in the figure, so that the test fixtures 901 may be lowered onto the predefined region 902 and positioned at a known distance from the fixed plate 904. The text fixtures 901 acting as actuating elements may have any appropriately structured surface so as to define a required shape of the actuator-sample contact. In FIG. 9, a cone-and-plate geometry is shown in which the actuator is a cone of a known apex angle. Other geometries, however, such as a parallel plate geometry in which the actuator is a flat disk parallel to the sample surface, may be employed as well. As in the previously-described embodiment, entrainment of viscous fluids is sufficient to keep the samples confined within a column capped by the actuator and the raised regions on the fixed plate 904. The test fixtures 901 are individually coupled to respective motors 910 via respective encoders 911. Advantageously, the predefined regions 902 contain respective force sensor elements.

Again referring to FIGS. 7 and 8, a strain field is generated across each sample by attaching the shear plate 701 to a translation stage which is not shown in the figures. This translation stage moves in the plane of the plate-sample contact at a controlled rate so as to approximate a sinusoidal displacement of a required amplitude and frequency. The fixed plate 704 remains fixed in position, resulting in a shear field extending through each sample. Appropriate translation stages providing the required displacement with appropriate amplitude and frequency are well-known to those skilled in the art.

In a further embodiment, a micromachined electrostatic drive can be associated with each sample, thereby permitting independent control of the strain field for each sample for extremely small displacements. Such actuators are preferably fabricated from silicon, silicon nitride, or any other suitable materials.

In the embodiment described with reference to FIG. 9, the motors 910 are actuated to provide a rotational displacement which may be provided to the samples in the form of a sinusoidal displacement of a desired amplitude and frequency or in the form of a continuous, i.e. a non-reciprocating shear at a defined shear rate. Compared to the translational embodiment described with reference to FIGS. 7 and 8, the rotational embodiment permits measurements under steady, shear conditions and can also be configured to operate as a controlled stress rheometer, as will be described below.

The translational embodiment as well as the rotational embodiment includes a shear stress sensor at each sample position. One version of this sensor element is described with reference to FIGS. 7 and 8 and consists of a micromachined silicon rectangle which is tethered to the surrounding silicon substrate by four micromachined silicon tethers. The surface of the rectangle lies in the plane of the surrounding silicon surface. Applying a shear stress to this rectangle by any of the means as described above generates a piezoelectric response in the four silicon tethers which can be detected by conventional electronic means such as a resistance bridge. Any variations in the geometry of this sensor element may be performed so as to permit it to be optimally used in all of the embodiments described above, i.e. the number of tethers, the shape of the silicon plate for receiving the sample, the location of the individual tethers, etc. may be adapted to the type of displacement required.

Although the operation of the embodiments of the parallel rheometer according to the present invention is described by means of a sinusoidal reciprocating motion in which, for example, an external processor directs the translation stage attached to the shear plate 701, or individually directs the micromachined electrostatic actuators, or individually directs the motors 910 to execute periodic motion in the plane of the plate-sample contact, other types of displacement such as triangular displacement of known amplitude and frequency, in which the strain rate is constant except at the turning points of the motion, and a motion which approximates a square wave of known amplitude and frequency may be employed as well. The raw data obtained from the sensor elements consists of the shear stress as a function of time and may be reduced and/or processed so as to yield a single amplitude for the shear stress waveform for each sample, wherein the data processing may be performed sequentially as well as in a parallel manner, depending on the computational ability of corresponding signal processing means. At any rate, signal processing speed is high compared to the mechanical time constant involved in the response of the sample so that a "quasi"-parallel output of measurement results is obtained, even if the sensor signals are sequentially processed.

It is also possible that the samples are subjected to a step shear and the resulting strain is determined as a function of time. This may be accomplished by providing the square wave displacement described above. Moreover, the embodiments described above may also be operated in a controlled stress mode. In this case, an external processor directs the actuator, i.e. the shear plate 701, the micromachined actuators, or the motors 910, to move so as to produce a certain shear stress within each sample. The displacement required to produce this stress is recorded with the aid of appropriate means, such as encoders 911. As before, the raw data consists of the displacement as a function of time which may be processed in any desired manner.

In other embodiments, the parallel rheometer of this invention preferably includes means for controlling and changing environmental conditions. This may be accomplished by mounting the embodiments in a temperature-controlled environment (not shown in the figures), permitting measurements to be made as a function of temperature, as a function at one or more temperatures, as a function of one or more temperature ramp rates, or as a combination of two or more of the preceding measurement criteria. In this case, temperature sensing can be provided by a thermocouple, thermistor or any other appropriate temperature-sensitive element attached to the shear plate or the fixed plate. Moreover, a thermocouple may be attached to each sensor or a standard micromachined resistor may be associated with each sensor.

Moreover, the embodiments of the parallel rheometer may be mounted in a pressure-tight enclosure (not shown in the drawings) permitting measurements to be made as a function of pressure, as a function of time at one or more pressures, as a function of pressure change rate, or as a combination of two or more of the preceding measurement criteria. Preferably, the enclosure is fitted with a purge valve enabling variation of gas composition and permitting measurements to be made as a function of composition, of time at a given composition, as a function of composition change rate, or as a combination of two or more of these criteria.

Moreover, either the shear or the sample plate may be fitted with one or more or an array of electrodes which serve to generate an electric field across each of the samples or across the samples as a whole. Measurements may be made as a function of field amplitude, field frequency, the rates of change of these two quantities, time at a given value of these two quantities, or a combination of two or more of these criteria.

In a further variation, either plate can include one or more or an array of coils which generate a magnetic field across each sample. Alternatively, the entire parallel rheometer may be placed between the poles of a large magnet or a pair of Helmholtz coils. In this case, the devices surrounding the sample, i.e. the shear plate 701 and the fixed plate 704 or 904 have to be constructed of a non-magnetic material in order to avoid eddy currents associated with the motion of the plates. Again, measurements may be made as a function of field amplitude, field frequency, the rates of change of these two quantities, time at a given value of these two quantities, or a combination of two or more of these criteria.

Preferably, in the embodiments having electrodes or coils generating a magnetic field, a force sensor element may be employed that is immune to electromagnetic noise, such as the sensor elements described below. However, the electronic sensor as described above with reference to FIGS. 7 and 8 may, nevertheless, be used as well.

Furthermore, in another embodiment, some or all of the environmental conditions delineated above may be varied simultaneously.

Next, a variety of force sensor elements are described which may be used in a rheometer, such as the above-described miniature rheometer and the parallel rheometer of the present invention, or any other appropriate rheometer known in the art.

Some of the sensor elements described below and referred to as "stress-optic" employ a material with a known stress-optic coefficient. This coefficient describes the birefringence, or anisotropic retardation of linearly-polarized light, of a material as a function of the applied stress per unit path length.

Figure 10:
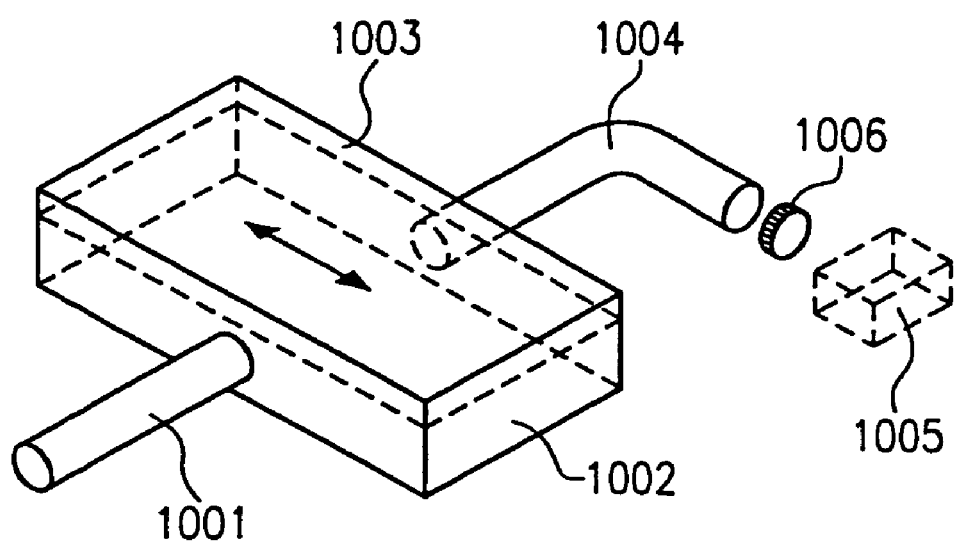
FIG. 10 is a schematic perspective view of an optical shear force sensing element which may be used in the parallel rheometer according to the present invention.

FIG. 10 is a schematic perspective view of the first embodiment of a stress-optic sensor according to the present invention. In FIG. 10, an optical fiber 1001 is attached to a block of stress-optic material 1002. The block 1002 is made of a suitable sensor material, including transparent plastics such as polymethyl methacrylate, suspensions of liquid crystals in a polymeric matrix, and certain silica glasses. A fixed plate 1003, preferably made of a rigid material such as stainless steel or aluminum is attached to the block 1002 in order to receive a sample. Opposed to fiber 1001 is a second fiber 1004 which is optically coupled to a detector element 1005. Fiber 1001 serves as an input fiber and is designed as a single mode optical fiber allowing the propagation of linearly polarized light. Accordingly, only linearly polarized light will enter block 1002, and the polarization direction of the input light will be changed in conformity with the shear force applied to the sample which is indicated by the arrow in FIG. 10. Preferably, optical fiber 1004, acting as an output fiber, is also designed as a single mode fiber with its polarization direction selected such as to be perpendicular to the polarization direction of the light output by fiber 1001. Preferably, the stress-optic material of block 1002 is prepared so as to exhibit zero birefringence in the absence of stress. Hence, substantially no light will be output by fiber 1004 and input into detector element 1005 when no shear stress is applied to a sample on plate 1003. Application of stress to the sample and thus to the sensor element alters the polarization of the light transmitted to block 1002 and produces a measurable signal at detector element 1005. The signal increases with increasing shear stress applied to the sample.

Alternatively, a polarizing element 1006 may be used between fiber 1004 and detector element 1005 when input fiber 1001 and output 1004 are of the same type, i.e. have the same polarization direction. Polarizing element 1006 is oriented such that its polarization direction is perpendicular to that of the fibers 1004 and 1001.

In a further alternative, the stress-optic material of block 1002 may be replaced by a short length of input fiber 1001 or output fiber 1004, which retards the polarization state of the transmitted light beam in response to a shear stress applied to the sample.

Figure 11:
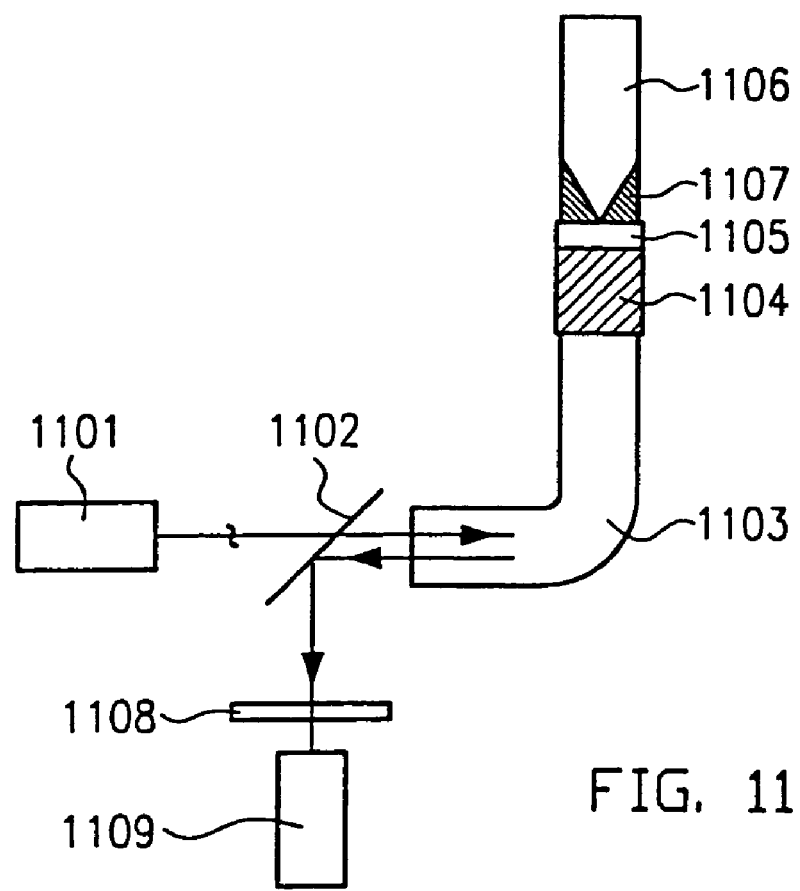
FIG. 11 respectively shows a further arrangement for optically detecting the shear force within a sample in a parallel rheometer according to the present invention.

FIG. 11 schematically shows a further embodiment of a stress-optic sensor element according to the present invention. In FIG. 11, a light source 1101, preferably a laser, emits linearly polarized light. The light emitted by light source 1101 passes through a half-mirror 1102 and is input into a multimode fiber 1103. A block of stress-optic material 1104 is attached to the other end of fiber 1103. The end of block 1104 opposing the fiber 1103 is provided with a sample plate 1105 which is preferably made of a rigid material such as stainless steel or aluminum and which is capable of reflecting light. Above sample plate 1105, a "moving" plate 1106, acting as an actuator, is positioned such that a sample 1107 is confined between sample plate 1105 and actuator 1106. In this embodiment, actuating element 1106 and sample plate 1105 exhibit a cone-and-plate geometry, however, any other appropriate geometry such as a parallel-plate geometry may also be used as previously mentioned. Further, in the optical path of light reflected by half-mirror 1102, a polarizing element 1108 is disposed in front of a detector 1109.

In operation, light source 1101, such as a laser, emits linearly polarized light which passes half-mirror 1102 and enters optical fiber 1103 which may be a multimode fiber. The light introduced into optical fiber 1103 is guided to the stress optic material of block 1104 and is reflected by sample plate 1105. The polarization direction of the light is altered due to a shear force applied to the sample 1107 by the actuating element 1106 which, in turn, induces a force in the stress-optic material 1104. The reflected light having the altered polarization direction due to its interaction with the stress-optic material is partly reflected by half-mirror 1102 and directed to polarizing element 1108 whose polarization direction is perpendicular to that of light source 1101. Hence, detector 1109 will detect a light intensity in response to the shear force prevailing in the stress-optic material 1104. Alternatively, optical fiber 1103 may be a single mode fiber with its polarization direction adjusted to be parallel with that of light source 1101. In this case, polarizing element 1108 may be omitted so that detector 1109 will detect a decreasing light intensity with increasing stress applied to the sample.

Figure 11A:
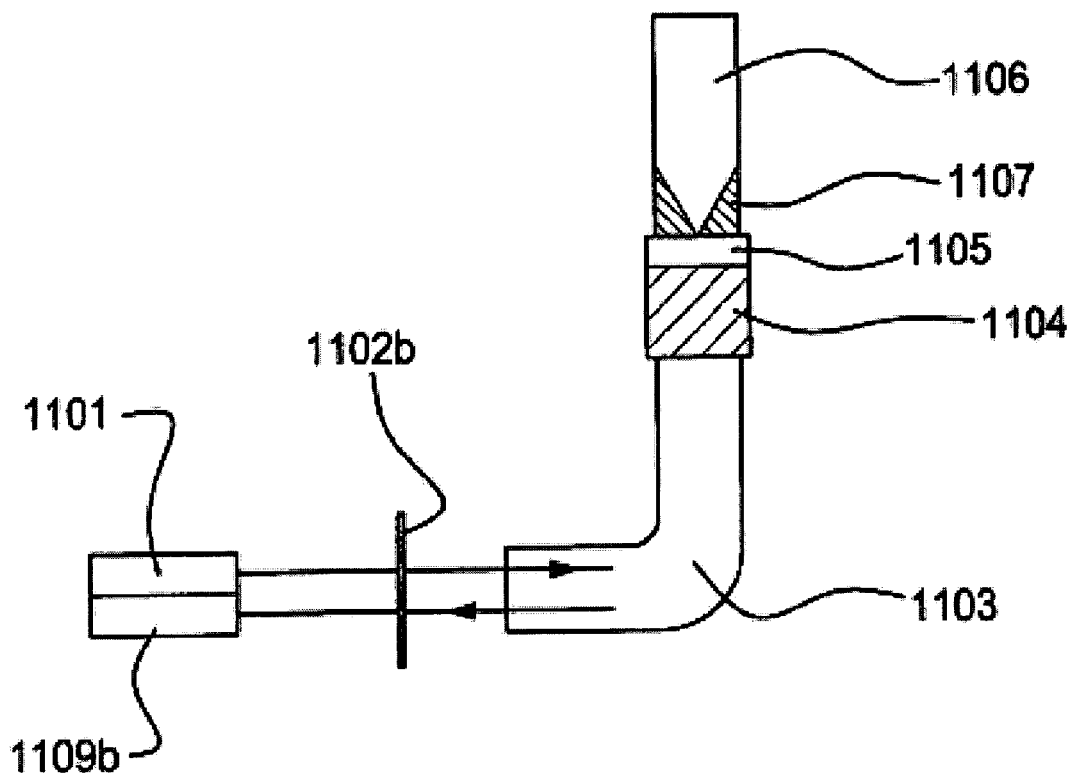
FIG. 11A shows an alternative arrangement for optically detecting the shear force within a sample in a parallel rheometer according to the present invention.

Alternatively, referring to FIG. 11A, light from light source 1101 is transmitted through a circular polarizer 1102b. Circularly polarized light is then introduced into the optical fiber and is guided to the stress optic material and reflected back by the sample plate. The polarization state of the light is altered due to the stress induced in the stress-optical material by shear applied to the sample by the actuating element. The reflected light having an altered polarization state due to its interaction with the stress-optic material is partly transferred back through the circular polarizer 1102b. Hence detector 1109b (positioned beside light source 1101) will detect a light intensity in response to the shear force prevailing in the stress-optic material.

Alternatively, the linearly polarized light may be directed onto the stress-sensor material at an oblique angle. Some fraction of the light is transmitted through the sensor material and is then reflected from the sample plate 1105 to pass back through the stress-optic material. In this case, the optical fiber 1103 may be omitted and some fraction of the reflected light is transmitted through the material-atmosphere interface and is incident onto the appropriately-placed polarizing element 1108 and detector 1109.

In a further embodiment not shown in the figures, using a single mode fiber optic the input fiber, the sensor material and the output fiber are combined into a single length of a single mode fiber optic. Applying a shear stress to a "sensor" section of this fiber optic rotates the polarization direction of the light passing through it due to the "stress optic" characteristics of the sensor section, as previously pointed out. The output section of this single mode fiber optic transmits only that portion of the light which has a polarization direction parallel to that transmitted by the input section. Thus, the intensity of light exiting the output section decreases with increasing shear stress applied to the sample.

Quantitative measurements may be facilitated by comparing the output of this single mode fiber optic to that transmitted by a second, unstressed length of a single mode fiber optic.

Suitable polarizers which may be employed in some of the above-mentioned embodiments include sheets of polarizing films, polarizing mirrors, and the direction of an initially polarized light beam onto the surface of the stress-optic material at the brewster angle. For the detectors used in the several embodiments mentioned above, films, photomultipliers, avalanche photodiodes, conductive photocells and CCD cameras may be employed.

The above-described embodiments of stress-optic sensors according to the present invention provide for ease of parallel data acquisition, immunity to electromagnetic noise, and great robustness at low temperatures.

Figure 12:
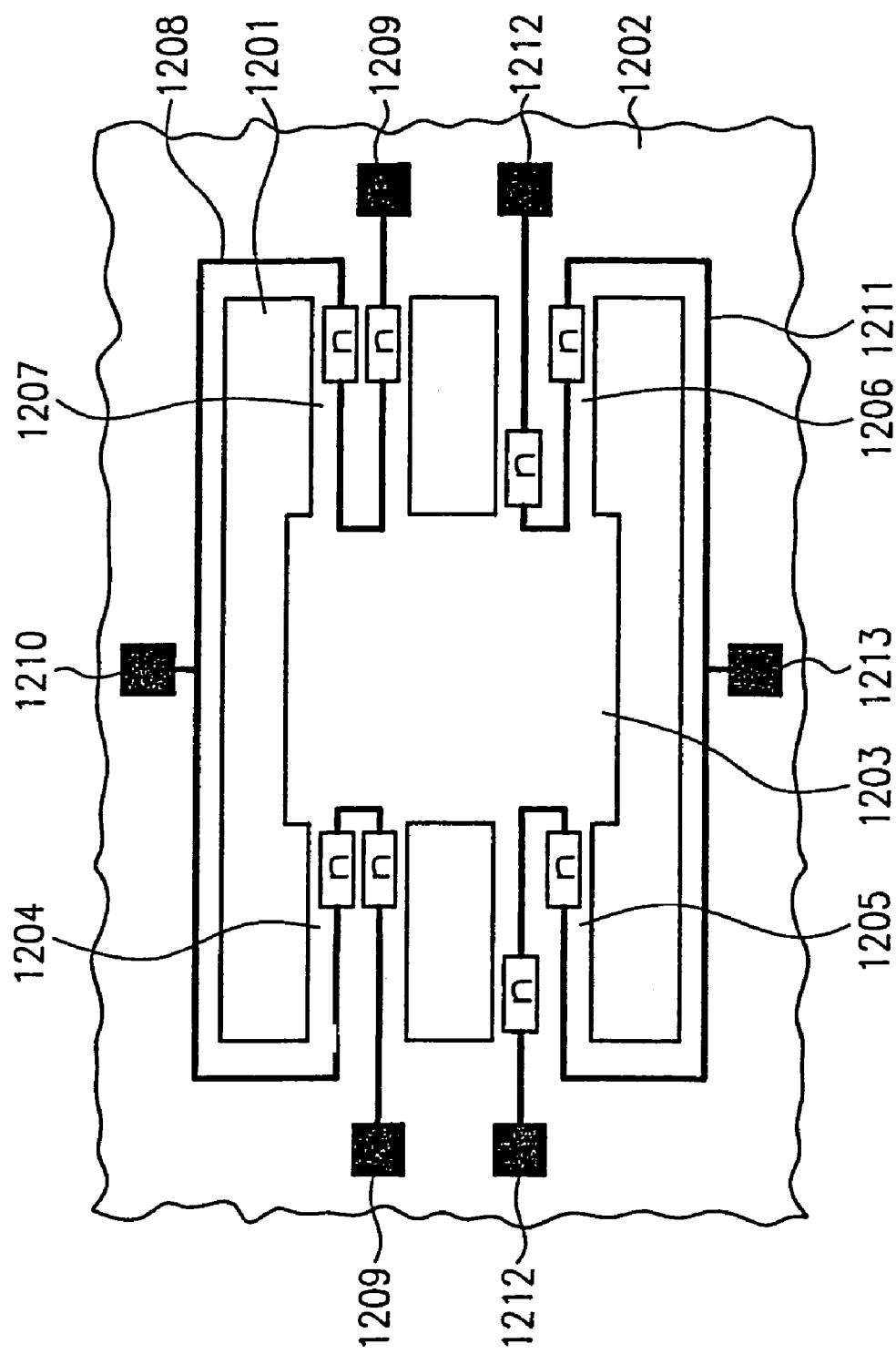
FIG. 12 schematically shows the structure of a sensor element which allows the simultaneous measuring of a shear force and a normal force applied to a sample, wherein the sensor element is preferably useable in a parallel rheometer according to the present invention.

With reference to FIG. 12, an improved force sensor element is described which allows the simultaneous measurement of a shear force and a normal force.

In FIG. 12, a recess portion 1201 is formed in a substrate 1202 comprising silicon or any other appropriate material such as silicon nitride or polyimide, etc., by standard micromachining manufacturing steps such as photolithography and etching. Within the recesses portion 1201, a rectangular plate 1203 is formed which is tethered by four tethers 1204, 1205, 1206 and 1207 to the substrate 1202. Each of the tethers 1204–1207 comprises two regions that have piezoresistive properties, which are shown as "N-doped" regions as indicated by "n" in the Figure. The tethers 1204 and 1207 are electrically connected by a wiring line 1208 which, in turn, is electrically connected to contact pads 1209 and 1210, respectively. Similarly, tethers 1205 and 1206 are electrically connected by a wiring line 1211 which, in turn, is electrically connected to contact pads 1212 and 1213, respectively. FIG. 12 is not to scale and the width of the tethers 1204–1207 is exaggerated in comparison with the side length of the plate 1203. In a preferred embodiment of the force sensor according to the present invention, the width of the tethers is about 80 µm and the side length of plate 1203 is in the range of one to several mm. The length of the tethers is about 1 mm and the length of a single piezoresistive area, i.e. of any N-doped regions in the surface layer of each tether, is about 300 µm.

As the skilled person will readily appreciate, the above dimensions may be varied in numerous manners so as to satisfy design and application requirements.

The force sensor according to the present invention is preferably manufactured as an array on a silicon substrate such as a lightly N-doped silicon wafer having a thickness of about 400 µm by means of conventional semiconductor manufacturing procedures which are well-known to the person skilled in the art. Hence, a detailed description of the various procedural steps in manufacturing the force sensor array will be omitted.

In operation, an input voltage is applied to the contact pads 1209 and an output voltage is obtained at contact pad 1210 which represents the middle terminal of a piezo-resistive bridge formed by the respective N-doped regions of the tethers 1204 and 1207, respectively. Similarly, an input voltage, possibly of the same amount as that applied to contact pads 1209, is applied to contact pads 1212 and an output voltage can be detected at contact pad 1213 which represents the middle terminal of a piezo-resistive bridge formed by the respective N-doped regions on the tethers 1205 and 1206, respectively. When a shear force is applied to the plate 1203, i.e. a force which, in the configuration of FIG. 12, is substantially oriented in the plane of the plate 1203 and normal to the axes of the tethers 1204–1207, so as to cause a slight displacement of the plate 1203, thereby generating a deformation of the tethers 1204 to 1207. The N-doped regions of tether 1207 are mirror-symmetrically arranged with respect to a vertical middle axis of plate 1203 so that the change in resistance of the tethers 1204 and 1207 will substantially cancel out each other. Accordingly, the voltage detected at contact pad 1210 substantially remains unchanged.

Contrary to this, on the tethers 1205 and 1206, N-doped regions are vertically arranged side by side so that upon application of a shear force, a maximum change of resistance in the doped regions of tether 1205 and 1206 will be obtained. Moreover, the doped regions on tether 1205 are inversely arranged to that of tether 1206 so that a maximum shift of the voltage detected at contact pad 1213 will occur. Accordingly, a shear force applied to the plate 1203 will provide a substantially unchanged output voltage on contact pad 1210, irrespective of the magnitude of displacement of plate 1203, and a maximally-shifted output voltage on contact pad 1213 depending on the magnitude of displacement. Hence, tethers 1205 and 1206 act as a shear force sensor element.

Similarly, when a force is applied to the plate 1203 which is directed perpendicular to the drawing plane of FIG. 12, the tethers 1204–1207 are deformed in such a way that the output voltage on contact pad 1210 is maximally shifted depending on the magnitude of displacement of plate 1203 in the direction perpendicular to the drawing plane, whereas the output voltage detected at contact pad 1213 remains substantially unchanged, irrespective of the magnitude of the displacement. Accordingly, the tethers 1204 and 1207 act as a normal force sensor element.

Although the force sensor which is able to simultaneously detect a shear force and a normal force has been described with reference to the embodiment as shown in FIG. 12, a variety of modifications may be performed still providing the same advantages as the embodiment described above.

For example, although the shear and normal force sensor element has been described to comprise four tethers, each including four appropriately-doped resistive regions, it is not necessary to provide four tethers per sensor plate. In certain circumstances, it may be preferable to have merely one tether for the normal force sensor element, or the shear force sensor element, or both. In this case, a corresponding displacement of the plate 1203 causes a deformation of the four-doped regions on each tether. When a shear force is applied, the deformation of the doped regions, which are arranged as shown, for example, on tether 1205 will lead to a change of resistance, which can be detected when a constant current is supplied to the tether. Similarly, a normal force applied to the tether will result in a change of resistance when the tether has an arrangement as shown with reference to tether 1204.

Moreover, in order to provide a stiffer behavior of the sensor element in responding to the shear force, it may be advantageous to arrange the tethers and doped regions thereon in such a way that the shear force is applied in the longitudinal direction of the tethers. For this case, tether 1207 of FIG. 12 will be doped as is shown in the Figure and tether 1206 will be doped as tether 1204 of FIG. 12, wherein contact pads 1209 and 1212 are electrically connected so as to serve as a middle terminal of the normal force resistant bridge. The shear force bridge formed of tethers 1204 and 1205 include, respectively, at least one doped region, wherein contact pads 1209 and 1212 are connected to serve as a shear force output. An input voltage common to the shear force sensor bridge and the normal force sensor bridge is applied at the contact pads 1210 and 1213.

Furthermore, the geometric arrangement of the tethers and the plate may be adapted so as to appropriately detect a rotational displacement applied to the plate 1203. This may include an arrangement in which the sample plate 1203 is tethered to the supporting substrate 1202 by diagonally-arranged tethers. Moreover, the plate 1203 may be formed in a circular shape and the tethers, provided in any appropriate number, may radially extend to the surrounding substrate.

The preferred layout of N-doped piezo-resistor regions shown in FIG. 12 is preferably aligned along the direction of maximum tension and preferably along the direction of maximum change in piezo-resistance, to get maximum sensitivity. For the embodiment shown in FIG. 12, the 100 direction is the direction of both maximum tension and maximum piezo-resistance change. Although the use of N-doped regions is shown, all N-doped regions may be replaced with P-doped regions. Also, the device alternatively may have different orientations of the piezo-resistor. For example, a P-doped piezo-resistor would preferably be aligned along the 110 direction, at 45 degree to the direction of longitudinal forces for maximum sensitivity. In alternative embodiments for the FIG. 12 embodiment of this invention, the N-doped regions may be replaced with any suitable piezo-resistive element, for example, piezo-resistive metal wires or doped polycrystalline silicon.

In order to achieve accurate measurement results, preferably each sensor element is calibrated by applying a defined normal force and shear force and detecting the corresponding output voltages so as to determine the degree of mixture of these two force components for each sensor device.

In an alternative embodiment, not shown in the figures, a device that has both piezo-resistive readout as well as capacitive electrodes to measure non-uniform forces acting on the plate may be used. In the preferred embodiment, four capacitive bond pad areas are placed at the four corners of the floating plate. Using both the piezo-resistor and the capacitive readouts, all the forces including the shear, the normal forces, and the rotational forces could be deconvolved. A skilled practitioner of the art can change the capacitor placement as well as change the capacitance area to maximize the device sensitivity.

Since the sensor element according to the present invention is preferably manufactured as an array of sensor elements on an appropriate substrate, this sensor element is advantageously used in combination with a parallel rheometer as previously described. Moreover, since these sensor elements may be produced in mass production at low cost, the sensor element may be designed as a disposable device so as to significantly facilitate sample preparation for a parallel rheometer. The inventive sensor element, however, may as well be used in combination with a single sample rheometer.

What is claimed is:

1. A method for measuring a fluid property, the method comprising
    providing a sensor that includes:
        a substrate having a recess formed therein,
        a plate disposed within the recess,
        a plurality of tethers suspendedly attaching the plate to the substrate for enabling reciprocating motion of the plate relative to the substrate, and
        at least one contact pad on the substrate adapted for electrical signaling communication with a power source and processing electronics,
    contacting the plate with a test fluid,
    oscillating the plate relative to the substrate, and
    determining at least one characteristic of the test fluid in response to contact with the plate.

2. The method of claim 1 wherein the sensor further comprises at least one electrode on the plate.

3. The method of claim 2 wherein the oscillating step comprises applying an electric field to the plate.

4. The method of claim 2 wherein the oscillating step comprises oscillating the plate within a magnetic field.

5. The method of claim 2 wherein the detecting step comprises detecting changes in rheological characteristic of the test fluid.

6. The method of claim 2 wherein the detecting step comprises detecting changes in shear or normal forces.

7. A fluid sensor comprising:
    a fluid sensing element, the fluid sensing element comprising:
        a substrate having a recess formed therein,
        a plate disposed within the recess, and
        a plurality of tethers suspendedly attaching the plate to the substrate for enabling oscillation of the plate relative to the substrate,
    at least one contact pad on the substrate, adapted for electrical signaling communication with a power source and processing electronics, and
    at least one electrode on the plate.

8. The sensor of claim 7 wherein the substrate, plate and tethers are micromachined.

9. The sensor of claim 7 wherein the substrate, plate and tethers comprise silicon.

10. The sensor of claim 7 further comprising at least one strain gauge located on one of the tethers, wherein the at least one strain gauge is connected to the at least one contact pad.

11. The sensor of claim 7 further comprising at least one strain gauge located on each of the tethers, wherein the strain gauges are connected to the at least one contact pad.

* * * * *